United States Patent [19]
Paton et al.

[11] Patent Number: 5,139,523
[45] Date of Patent: Aug. 18, 1992

[54] ARTIFICIAL LIMB SOCKET APPARATUS

[76] Inventors: Matthew T. Paton; Judith T. Paton, both of P.O. Box 343, 827 Main St., W. Harwich, Mass. 02671

[21] Appl. No.: 729,171

[22] Filed: Jul. 12, 1991

[51] Int. Cl.$^5$ ............................. A61F 2/60; A61F 2/74
[52] U.S. Cl. ........................................ 623/37; 623/26; 623/33
[58] Field of Search ...................................... 623/33–37, 623/57, 26, 27

[56] References Cited

U.S. PATENT DOCUMENTS

| | | | |
|---|---|---|---|
| 2,790,180 | 4/1957 | Hauser | 623/34 |
| 3,889,301 | 6/1975 | Bonner | 623/37 |
| 4,300,245 | 11/1981 | Saunders | 623/35 |
| 4,468,821 | 9/1984 | Saunders | 623/35 |

FOREIGN PATENT DOCUMENTS

| | | | |
|---|---|---|---|
| 0019612 | 11/1980 | European Pat. Off. | 623/37 |
| 2729800 | 1/1979 | Fed. Rep. of Germany | 623/34 |
| 0625705 | 9/1978 | U.S.S.R. | 623/57 |

Primary Examiner—Randall L. Green
Assistant Examiner—D. Willse
Attorney, Agent, or Firm—Leon Gilden

[57] ABSTRACT

An apparatus for mounting a socket above the knee of an amputee, wherein the socket is arranged for mounting a prosthesis to a lower terminal end thereof. The sleeve includes an internal cage formed of rigid rods, including hook members imbedded within a semi-spherical sleeve support, with the cage encased in a polymeric covering. A vent is provided through the sleeve support for venting interiorly of the socket. The socket may further include pneumatic chambers for enhanced comfort in support of the socket.

2 Claims, 4 Drawing Sheets

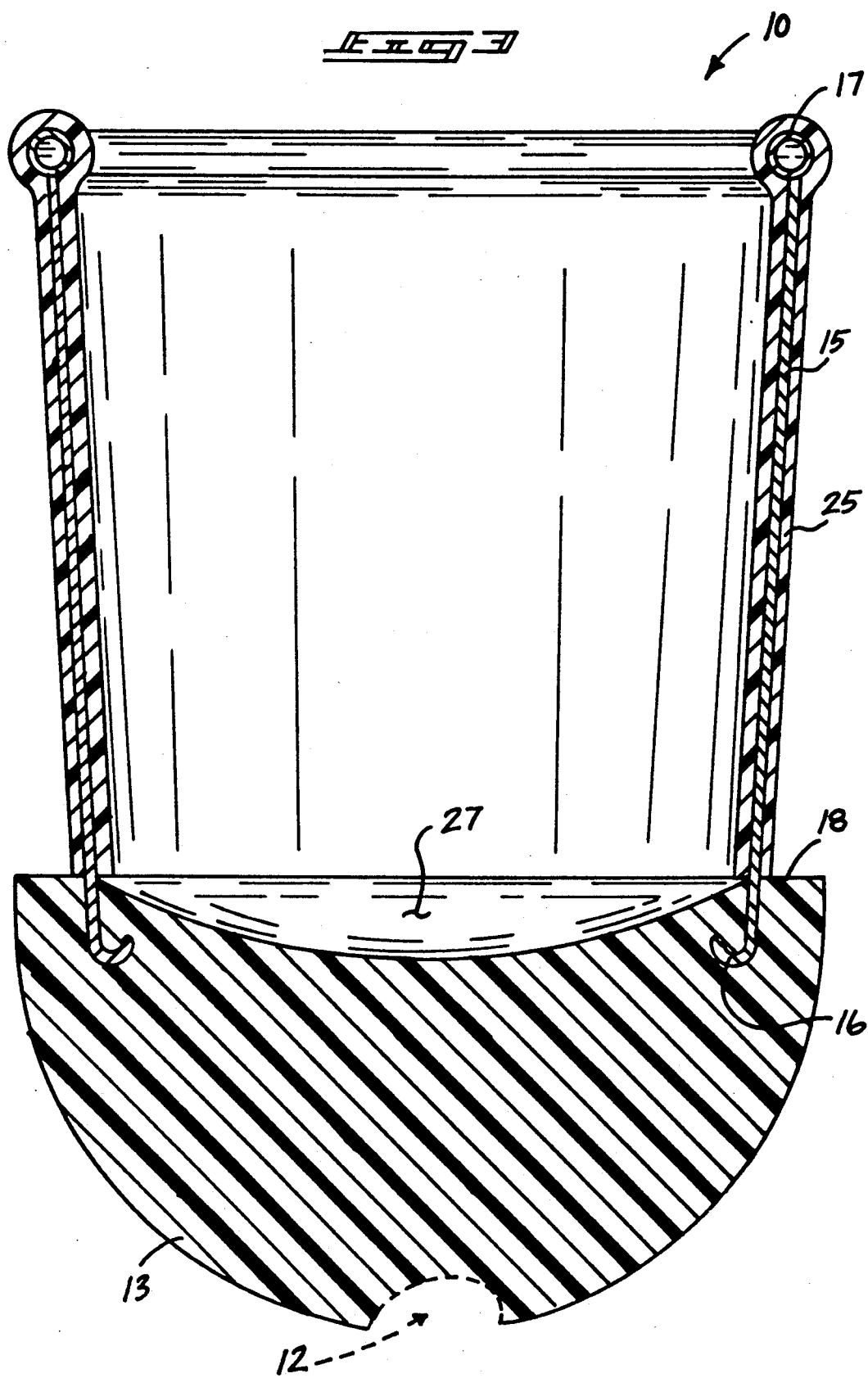

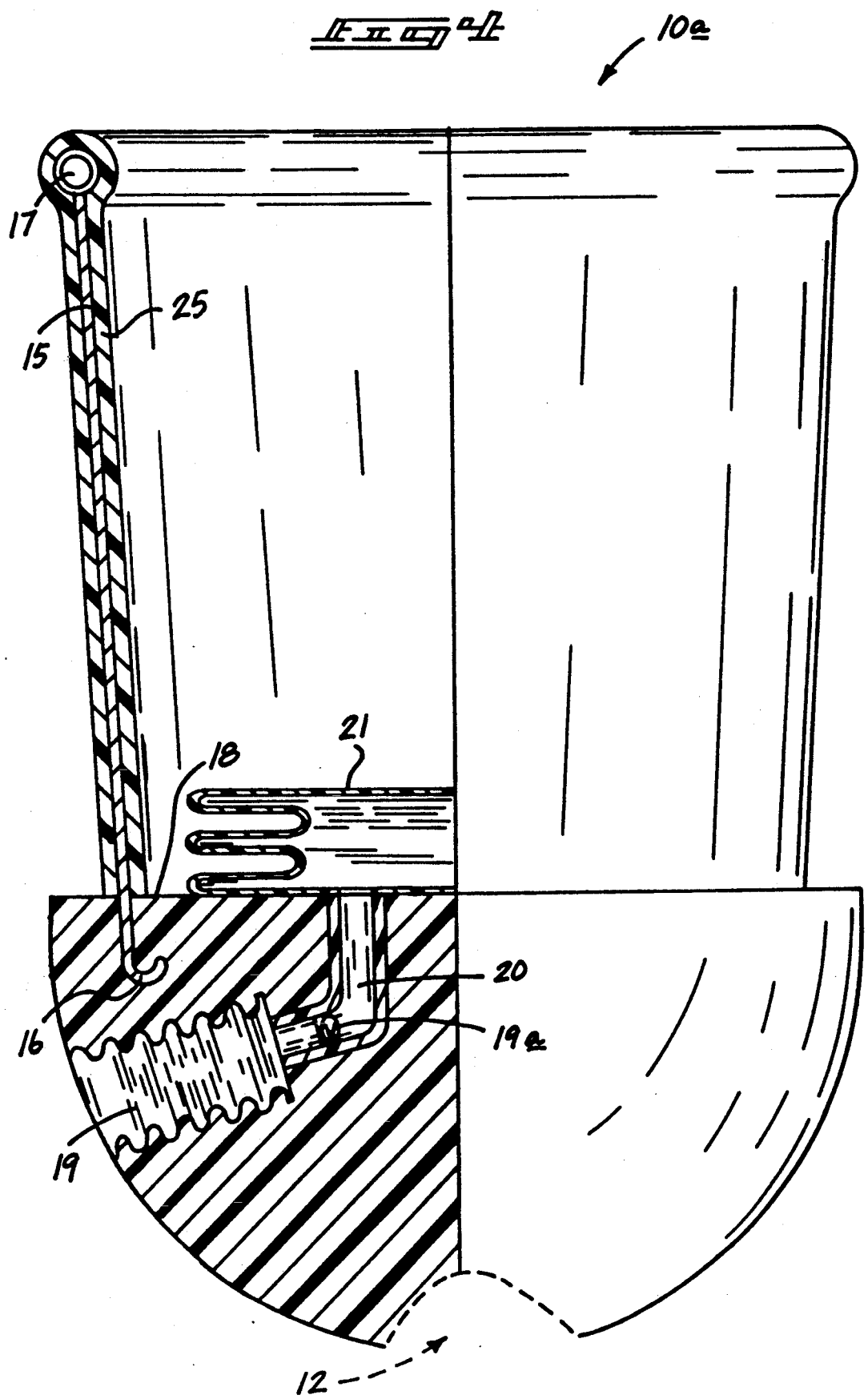

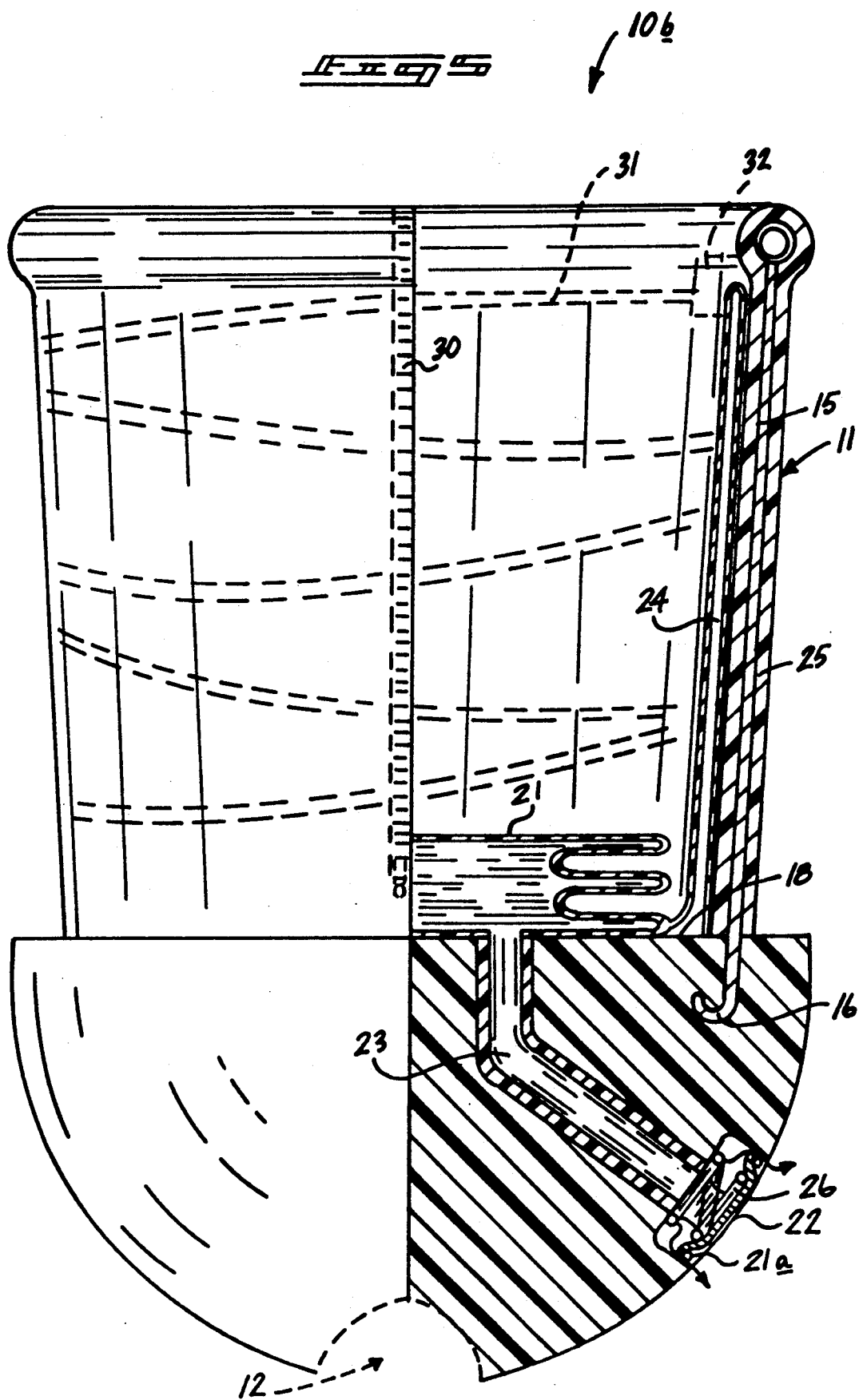

ARTIFICIAL LIMB SOCKET APPARATUS

BACKGROUND OF THE INVENTION

1. Field of the Invention

The field of invention relates to artificial limb attachment devices, and more particularly pertains to a new and improved artificial limb socket apparatus wherein the same is arranged for mounting to an amputation in an above-the-knee amputee.

2. Description of the Prior Art

Mounting of prosthesis devices to an amputated portion of a leg requires careful mounting and securement to an amputated limb, as well as protection of the limb against a prosthesis. Prior art devices in this regard may be found in U.S. Pat. No. 4,479,272 to Beldzisky setting forth an elongate sheath mounted to an amputation, wherein the sheath is arranged for securement to the amputation for mounting a prosthesis relative thereto.

U.S. Pat. No. 2,202,598 to Peterson sets forth a sock member of flexible construction for mounting to an amputated portion of a limb.

U.S. Pat. No. 3,461,464 to Lindgren sets forth an artificial limb formed with interchangeable leg sections, including length adjustment means associated therewith.

U.S. Pat. No. 1,305,573 to Kannel sets forth an example of a socket for mounting to an amputation for subsequent mounting to a prosthesis.

As such, it may be appreciated that there continues to be a need for a new and improved artificial limb socket apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of artificial limb apparatus now present in the prior art, the present invention provides an artificial limb socket apparatus wherein the same is arranged for mounting to an amputation of an above-the-knee amputee. As such, the general purpose of the present invention, which will be described subsequently in greater detail, is to provide a new and improved artificial limb socket apparatus which has all the advantages of the prior art artificial limb apparatus and none of the disadvantages.

To attain this, the present invention provides an apparatus for mounting a socket above the knee of an amputee, wherein the socket is arranged for mounting a prosthesis to a lower terminal end thereof. The sleeve includes an internal cage formed of rigid rods, including hook members imbedded within a semi-spherical sleeve support, with the cage encased in a polymeric covering. A vent is provided through the sleeve support for venting intertiorly of the socket. The socket may further include pneumatic chambers for enhanced comfort in support of the socket.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved artificial limb socket apparatus which has all the advantages of the prior art artificial limb apparatus and none of the disadvantages.

It is another object of the present invention to provide a new and improved artificial limb socket apparatus which may be easily and efficiently manufactured and marketed.

It is a further object of the present invention to provide a new and improved artificial limb socket apparatus which is of a durable and reliable construction.

An even further object of the present invention is to provide a new and improved artificial limb socket apparatus which is susceptible of a low cost of manufacture with regard to both materials and labor, and which accordingly is then susceptible of low prices of sale to the consuming public, thereby making such artificial limb socket apparatus economically available to the buying public.

Still yet another object of the present invention is to provide a new and improved artificial limb socket apparatus which provides in the apparatuses and methods of the prior art some of the advantages thereof, while simultaneously overcoming some of the disadvantages normally associated therewith.

Still another object of the present invention is to provide a new and improved artificial limb socket apparatus wherein the same is arranged for comfort and convenience of mounting to an amputation for subsequent securement of a prosthesis thereto.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an orthographic cross-sectional illustration of the instant invention.

FIG. 4 is an orthographic partial cross-sectional illustration of a modification of the instant invention.

FIG. 5 is a cross-sectional illustration of a further modified aspect of the instant invention.

DESCRIPTION OF THE PREFERRED EMBODIMENT

Figure 1:
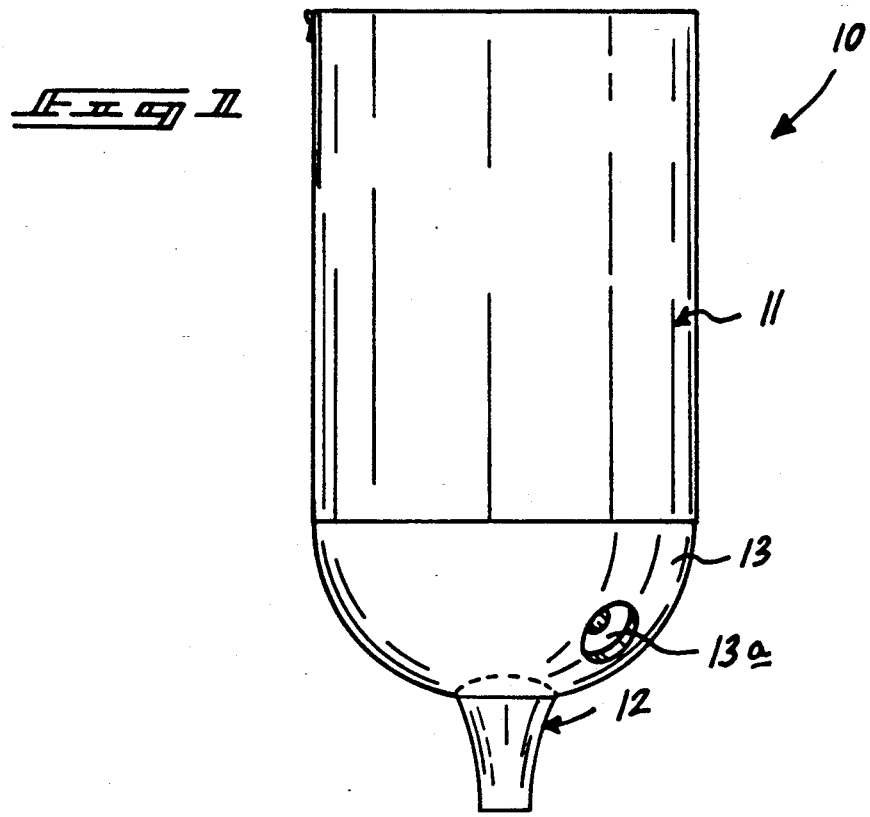
FIG. 1 is an orthographic side view of the instant invention.
Figure 2:
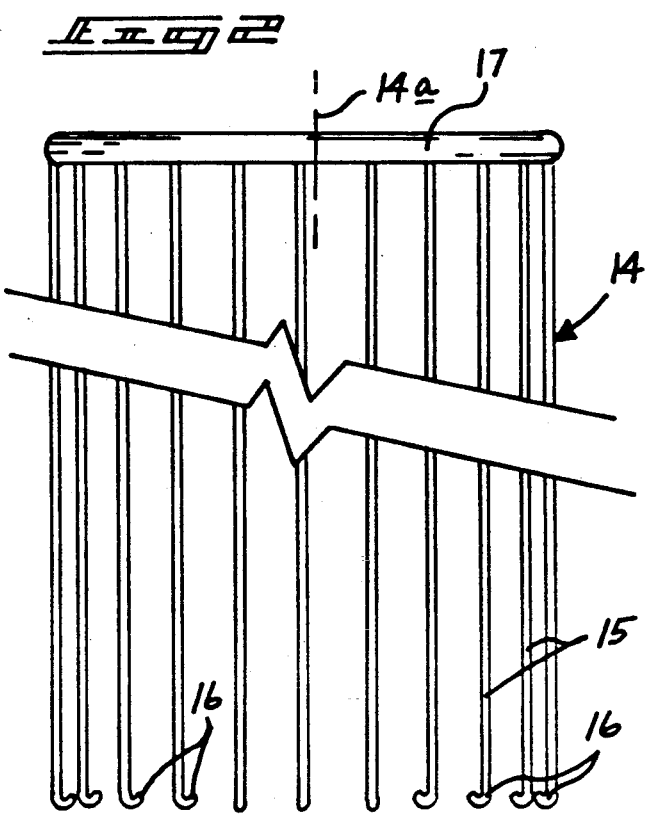
FIG. 2 is an orthographic side view of a cage structure utilized by the instant invention.

With reference now to the drawings, and in particular to FIGS. 1 to 5 thereof, a new and improved artificial limb socket apparatus embodying the principles and concepts of the present invention and generally designated by the reference numerals 10, 10a, and 10b will be described.

More specifically, the artificial limb socket apparatus 10 of the instant invention essentially comprises a sleeve 11 of a generally cylindrical configuration mounted to a polymeric semi-spherical sleeve support 13, wherein the sleeve support 13 includes a planar surface coaxially aligned relative to an axis 14a of the sleeve 11. The sleeve 11 includes a rigid cylindrical cage 14 defining a framework of a generally cylindrical configuration, wherein the cage 14 of a generally rigid construction is mounted to the sleeve support 13 that in turn includes a prosthesis connection member 12 of a desired configuration mounted thereto. The cage 14 is defined by a series of equally spaced elongate rods 15 formed of a rigid material, such as stainless steel, rigid polymerics, and the like, with a lower terminal end defining a hook shaped end 16, with each hook shaped end directed radially and interiorly of the cylindrical cage 14. Each upper terminal end of the rods 15 is fixedly and orthogonally mounted to a cylindrical band 17. The cylindrical band 17 is orthogonally oriented relative to the axis 14a. Reference to FIG. 3 illustrates that the sleeve support planar bottom surface 18 includes a receiving cavity 27 for receiving an amputation therewithin.

It is desirable that in use the amputee may form a cast of the amputation for subsequent fitting to the sleeve 11.

A polymeric covering 25 is coextensively mounted about the cage 14 defining a continuous interior cylindrical wall surface and a continuous exterior cylindrical wall surface. If required, the sleeve 11 may further be formed as a conical configuration for better adaption to an amputation, but also formed along a single central axis 14a.

FIG. 4 illustrates a modified socket apparatus 10a, including an expandable pneumatic bladder 21 mounted to the bottom surface 18 within the sleeve 11 and cooperative through a channel 20 to effect inflation selectively of the bladder 21 by use of an air pump 19 that in turn is operative through a one-way valve 19a. For enhanced comfort, the bladder 21 is formed in pneumatic communication with a surroundingly positioned side wall bladder 24 that is coextensively formed to the interior surface of the sleeve 11 to accommodate deviation formation of the sleeve 11 and its securement and comfort in use by an individual. Further, a pressure release web 22 is formed through an exterior surface of the sleeve support 13. The sleeve support 13 may utilize a vent 13a, but in lieu of the vent 13a, the pressure relief organization, including the web 22, is cooperative through a pressure release channel 23, whereupon manual pressure directed against the web 22 displaces the web from a surrounding "O" ring seal 21a formed within a forward cavity at an entrance to the pressure release channel 22 to permit selective release of pressure within the bladder structure. A spring 26 normally biases the web 22 into a sealing relationship relative to the "O" ring 21a.

The embodiment of FIG. 5 also illustrates the use of a zipper 30 that is directed longitudinally of the covering 25 permitting access through the cage 14 and the covering 25 for enhanced ease of cleaning of the structure and maintenance thereof. The cleaning procedure permits enhanced and prolonged usage of the device providing a sanitary socket construction. Also, as illustrated in FIG. 5, a serpentine heating coil 31 operative through a replacement battery 32 mounted within the wall of the covering 25 is provided for added comfort to a wearer of the socket construction of the invention. The heating element is arranged to encompass a major portion of the covering 25 and not interfere with operation of the zipper 30 in use.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. An artificial limb socket apparatus comprising,
   a cylindrical sleeve including a lower terminal end, the sleeve defined along a sleeve axis, and
   the sleeve mounted at said lower terminal end to a semi-spherical sleeve support, the sleeve support including a planar top surface, and
   the sleeve including a cage framework, the cage framework including a plurality of equally spaced elongate rods, a lower terminal end of each said elongate rod being embedded within the sleeve support, and each lower terminal end of the elongate rods includes a hook shaped member radially directed interiorly of the cylindrical sleeve, and an upper terminal end of each rod being fixedly mounted to a support band, and
   a polymeric covering coextensively formed about the rods and the band to define a continuous interior sleeve wall and a continuous exterior sleeve wall, and the planar top surface includes a pneumatic bladder mounted thereon interiorly of the sleeve, and the bladder in pneumatic communication with a first channel, the first channel directed from the bladder through the sleeve support, and a manual pump member mounted within the support in communication with the first channel to effect selective inflation of the bladder, and a further bladder in pneumatic communication with the pneumatic bladder, wherein the further bladder is in contiguous and coextensive communication with the interior surface of the sleeve, whereupon inflation of the pneumatic bladder effects simultaneous inflation of the further bladder, and a second channel, the second channel in pneumatic communication with the bladder directed through the planar bottom surface and extending through the sleeve support, and a forward cavity in communication with a terminal end of the second channel, with the forward cavity including a release web, the release web biased into a pneumatically sealed relationship with an "O" ring secured within the forward cavity to maintain pressure within the bladder and the further bladder, and a biasing spring mounted between the web and the second channel within the forward cavity, with the release web displaceable against the biasing spring to effect release of pressure of the bladder and further bladder upon displacement of the release web relative to the "O" ring, and the polymeric covering includes a zipper member longitudinally directed through the polymeric covering permitting access interiorly of the covering and directed between the rods for enhanced ease of cleaning of the sleeve.

2. An apparatus as set forth in claim 1 further including a serpentine heating member directed through the sleeve for selective heating of the sleeve during use.

* * * * *